US006408256B1

(12) United States Patent
Hittle et al.

(10) Patent No.: US 6,408,256 B1
(45) Date of Patent: Jun. 18, 2002

(54) APPARATUS AND METHOD FOR THERMAL EVALUATION OF ANY THIN MATERIAL

(75) Inventors: Douglas C. Hittle, Fort Collins, CO (US); Tifani L. André, Kentfield, CA (US)

(73) Assignee: Colorado State University Research Foundation, Fort Collins, CO (US)

( * ) Notice: Subject to any disclaimer, the term of this patent is extended or adjusted under 35 U.S.C. 154(b) by 53 days.

(21) Appl. No.: 09/677,428

(22) Filed: Oct. 2, 2000

Related U.S. Application Data

(60) Provisional application No. 60/157,679, filed on Oct. 1, 1999.

(51) Int. Cl.[7] ............................. G01K 1/00; G01K 13/00
(52) U.S. Cl. ........................ 702/130; 702/132; 702/136; 374/179; 73/649
(58) Field of Search ................................. 702/130, 132, 702/136, 45, 50, 100, 104; 374/100, 174–176, 178–179; 73/25.01, 25.03, 54.43, 61.46, 61.54, 649, 658

(56) References Cited

U.S. PATENT DOCUMENTS

| 3,688,558 | A | | 9/1972 | Tixier ............................. 73/15 |
| 4,553,852 | A | | 11/1985 | Derderian et al. ............. 374/1 |
| 4,756,958 | A | | 7/1988 | Bryant et al. ............. 428/320.2 |
| 4,839,667 | A | * | 6/1989 | Murakami et al. .......... 347/220 |
| 4,908,238 | A | | 3/1990 | Vigo et al. ................... 427/389 |
| 5,067,094 | A | * | 11/1991 | Hayes .......................... 702/51 |
| 5,643,485 | A | * | 7/1997 | Potter et al. ................. 219/430 |
| 5,711,607 | A | * | 1/1998 | Bernstein .................... 374/179 |
| 5,749,259 | A | | 5/1998 | Hamouda et al. ............. 75/159 |
| 5,885,475 | A | | 3/1999 | Salyer .......................... 252/70 |
| 6,123,097 | A | * | 9/2000 | Truong et al. ............... 137/334 |

OTHER PUBLICATIONS

*American Society for Testing and Material,*Standard D 518, "Standard Test Method for Thermal Transmittance of Textile Materials", pp. 379–386, 1998.

* cited by examiner

*Primary Examiner*—Bryan Bui
(74) *Attorney, Agent, or Firm*—Macheledt Bales LLP

(57) ABSTRACT

An apparatus and method for evaluation of a material having a first and second contact-surface. The apparatus includes a computer-controlled thermally-variable central element comprising a first and second outer surface, at least one outer surface having at least one temperature sensor thereon. Facing the first outer surface is a first exterior surface of a first thermally-variable side element, and facing the second outer surface is a second exterior surface of a second thermally-variable side element. A mechanism is a second exterior surface of a second thermally-variable side element. A mechanism is included that operates to move at least the first exterior surface toward the thermally-variable central element to apply a generally uniform pressure against the material contact-surfaces once the material has been so positioned.

20 Claims, 4 Drawing Sheets

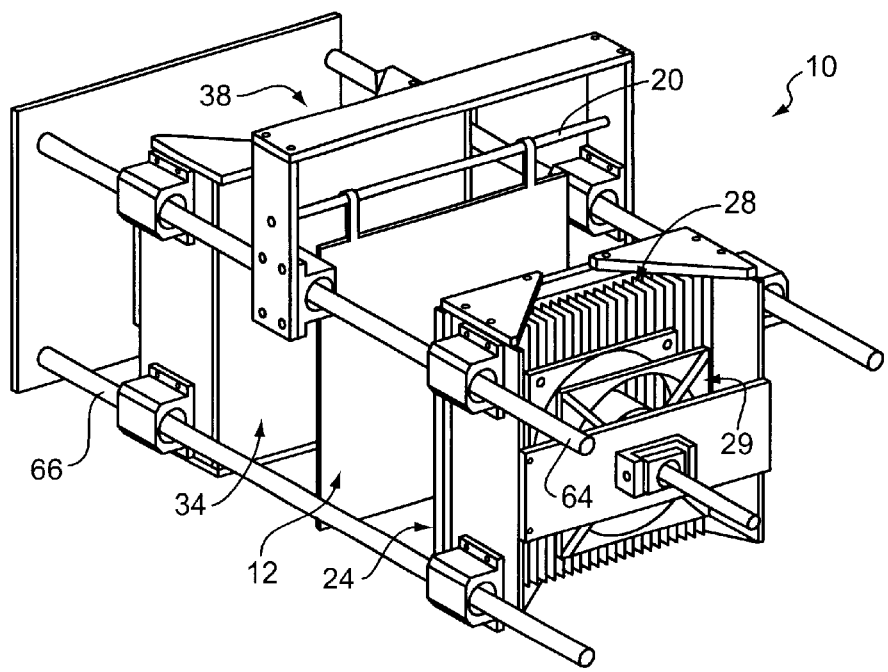
FIG. 3
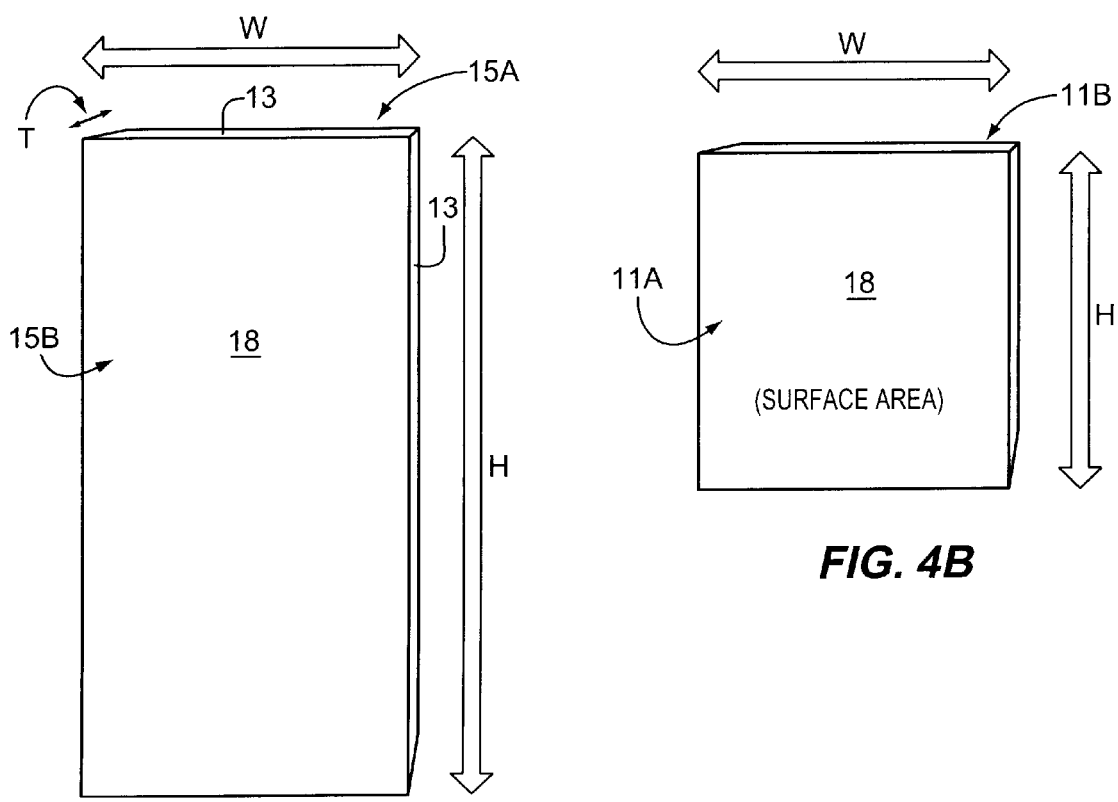
FIG. 4A
FIG. 4B

APPARATUS AND METHOD FOR THERMAL EVALUATION OF ANY THIN MATERIAL

Background of the Invention

This application claims priority under 35 U.S.C. 119(e) and 37 C.F.R. §1.78 to Provisional Patent Application U.S. Pat. No. 60/157,679 filed Oct. 1, 1999.

In general, the present invention relates to the evaluation of materials that have dynamic thermal-, moisture-, and/or energy-storage properties, such as materials containing a 'phase change' component (whether it is as microspheres filled with phase change material, microcapsules containing phase change material, as phase change material incorporated into the structure of the fibers, as hollow fibers or pores filled with phase change material, phase change material impregnated upon non-hollow fibers, as a laminate or coating with a phase change layer, etc.) and other materials used in moisture and/or thermal management systems for apparel, bedding, drapery, upholstery, flooring/carpets, ceilings, wall-coverings, walls (including interior and supporting walls of ground vehicles, aircraft, watercrafts, etc.), wood planks, drywall, and so on. More particularly, the invention relates to a new evaluation apparatus, method for evaluating materials, including thermally-dynamic materials, and an associated novel metric (herein referred to as a temperature regulating factor, TRF) for comparing thermal-regulating ability of such materials that more-readily simulates the dynamic, or transient, nature of associated 'real' environments in which these materials are used (whether the simulated environment is comprised of a transient response that is generally random, periodic, or some combination thereof).

The development of 'smart' materials to better thermally regulate an environment (be it the microclimate of human, his/her pet, or farm animal in proximity to cloth, the interior of a vehicle or aircraft, inside of living/office spaces, research laboratories, and production facilities, and so on) has far outpaced the conventional methods used to evaluate such materials to the point of making conventional testing methods and the associated quantities used for comparison, nearly obsolete. High performance materials continue to be evaluated using known techniques whereby the material is exposed to a static environment—test results focus simply on insulation.

For example, in the textile arena, the conventional method for measuring thermal properties of textiles is described in the American Society for Testing and Materials' (ASTM) Standard D 1518 entitled, "Standard Test Method for Thermal Transmittance of Textile Materials." This standard is currently employed to determine the overall thermal transmittance coefficients due to the combined action of conduction, convection, and radiation for dry textile specimens. The test apparatus consists of a 'guarded' hot plate assembly enclosed in an environmental chamber. Fabric is wrapped around the guarded hot plate, which is intended to simulate human skin. The top hot plate, its 'guard' (a second hot plate) and fabric are placed in an environmental enclosure, which is maintained at a cooler temperature than the guarded hot plate, between 4.5 and 21.1° C. (40–70° F.). The hot plate is maintained between 33.3 and 35° C. (92–95° F.). The guard is necessary to ensure that thermal energy is transferred out of the guarded hot plate assembly through the fabric side, only. This test procedure was designed to create a temperature gradient through the fabric, allowing one to measure a value for rate of heat transfer from the hot plate to the opposite, or outwardly directed, side of the fabric. This rate of heat transfer has been used to characterize the insulative capability of the fabric sample. As one can appreciate, this complicated ASTM D 1518 test simply cannot appropriately characterize thermally-dynamic materials used and/or under development.

The ASTM textile test apparatus and protocol have some known disadvantages (which give inconsistent results): The fabric oftentimes makes poor contact with the guarded hot plate; the convection coefficient over the fabric may vary if appropriate measures of control are not employed which affects results; and especially since the protocol requires close control of several of the variable test parameters, reliability and accuracy of results obtained using ASTM D 1518 have been shown by researchers to vary. Furthermore, since research and product analysis has focused on measures of insulation, ASTM D 1518 is strictly limited to simple insulation measurements, it does not simulate real environmental conditions, and cannot adequately measure the enhanced thermal regulation performance obtained by adding phase change materials to a textile. Other than the ASTM D 1518 method, no other U.S. standard method for evaluating the thermal regulating ability/properties of textiles, let alone thermally-dynamic materials, is known by applicants.

Therefore, a new useful apparatus, method and associated metric is needed for the comparative evaluation of materials, whether the materials have a dynamic thermal-, moisture-, and/or energy-storage component designed for expected use in a 'transient' environment. Without reasonable, accurate, and cost-effective solutions at hand for evaluating materials in a timely, reproducible manner, it has been very difficult to make useful comparison-evaluations of products fabricated using the materials. Unlike the conventional systems currently in use, the innovative apparatus, and associated method and metric for characterizing the thermal (or energy) regulating ability of the material under evaluation (be it a flexible textile/fabric, carpet, wall laminate, fiberglass, wood product, and so on) more-accurately simulates the conditions under which such dynamic materials are used—giving much more accurate results than methods/instruments currently-available. In the spirit of design goals contemplated hereby, many different types of materials, including those with a dynamic thermal-, moisture-, and/or energy-storage component can be evaluated utilizing the instant invention, as will be appreciated.

SUMMARY OF THE INVENTION

It is a primary object of this invention to provide an apparatus for evaluation of a material having a first and second contact-surface, and associated method and metric for comparative characterization of the thermal-, moisture-, energy-regulating ability of a material under evaluation. Such an apparatus and method include a computer-controlled thermally-variable central element having a first and second outer surface, at least one of which may have a temperature sensor thereon, located between a first and second thermally-variable side element whereby the material can be positioned between the central element and each of these thermally-variable side elements. A multitude of materials, whether containing a dynamic moisture-, thermal-, and/or other type of energy-storage component, can be evaluated using the innovative apparatus and method.

The advantages of providing the new apparatus, method, and metric, and the very distinguishing features thereof, as described and supported can be readily appreciated.

(a) The invention affords a means by which the thermal-regulating ability of materials can be evaluated for comparative analysis, regardless of the type of material, its size/thickness, final shape, or end-use, the results of the evaluation can be used to provide information that can be compared with other materials.

(b) The apparatus and method more-readily simulates the dynamic, or transient, nature of associated 'actual' environments in which a material under evaluation are used (whether the simulated environment is comprised of a transient response that is generally random, periodic, or some combination thereof).

(c) The apparatus and method of the invention may be used to evaluate a multitude of materials of a wide variety of sheet stock/material, such as fabrics (including any flexible material made of an individual component or combination of cloth, fibers, polymeric film, sheeting, or foam, metallic foil or coating, ceramic/glass substrate, etc.—whether laminated or coated—used in carpets, apparel, bedding, drapery, upholstery, and so on), drywall and other wall laminates, wood products and other sheet stock made of a cellulous material, fiberglass, and so on. Once the pressure regulator has been calibrated to apply the preselected pressure to the surface of a material, one apparatus may accommodate many different material samples (as a single sheet or two separately-hung sheets).

(d) The apparatus and method of the invention provide comparative results in a cost-effective manner without requiring that conditions surrounding the apparatus be so closely regulated/controlled, yet automatically control values measured and tracked, such as the magnitude and preselected variability of thermal energy/flux into the central element, surface temperature of both outer surfaces of the central as well as the exterior surfaces of both side elements, and duration of evaluation, using currently available computer processing and data acquisition equipment.

Briefly described, once again, the invention includes an apparatus and method for evaluation of a material having a first and second contact-surface. The apparatus includes a computer-controlled thermally-variable central element comprising a first and second outer surface, at least one outer surface having at least one temperature sensor thereon. Facing the first outer surface is a first exterior surface of a first thermally-variable side element, and facing the second outer surface is a second exterior surface of a second thermally-variable side element. A mechanism is included that operates to move at least the first exterior surface toward the thermally-variable central element to apply a generally uniform pressure against the material contact-surfaces once the material has been positioned. A particular material is preferably positioned for evaluation (whether as a single large piece, or as two individual pieces) between the central element's first outer surface and the first exterior surface, and between the central element's second outer surface and the second exterior surface. A computer processor in communication with a computer memory can be used for controlling the central and side elements. As defined for reference purposes, the first and second outer surfaces have a respective measured temperature value of $T_{High\text{-}1}$ and $T_{High\text{-}2}$, and the first and second exterior surfaces have a respective selected temperature value of $T_{Low\text{-}1}$ and $T_{Low\text{-}2}$.

Additional further distinguishing features include: A first heat sink in proximity to a backside of the first side element, a second heat sink in proximity to a backside of the second side element, and a linear bearing upon which the central element, the first and second side elements, and the respective heat sinks are mounted. The thermally-variable central element can comprise a relatively flexible plate-like structure oriented generally vertically. The thermally-variable side elements can comprise a metal alloy plate-like structure, whereby respective first and second exterior surfaces are contoured to mate with respective first and second outer surfaces of the central element, when in contact. The mechanism for moving can comprise a surface-contact pressure regulator and a lever for moving the first heat sink and first side element along the linear bearing. A first thermoelectric cooler can be sandwiched between the first side element and the first heat sink, and a second thermoelectric cooler can be sandwiched between the second side element and a second heat sink.

The method characterized comprising the steps of: positioning the material between a first outer surface, at a temperature $T_{High\text{-}1}$, of a computer-controlled thermally-variable central element and a first exterior surface of a first thermally-variable side element, and between a second outer surface, at a temperature $T_{High\text{-}2}$, of the central element and a second exterior surface of a second thermally-variable side element; moving at least one side element toward the central element to apply a generally uniform pressure against the material contact-surfaces; and measuring a temperature value of the first and second exterior surfaces, respectively $T_{Low\text{-}1}$ and $T_{Low\text{-}2}$, whereby $T_{High\text{-}1}$ and $T_{High\text{-}1}$ are maintained higher than values $T_{Low\text{-}1}$ and $T_{Low\text{-}2}$. One can control $T_{Low\text{-}1}$ and $T_{Low\text{-}2}$, through feedback carried out using a computer processor. The energy input into the central element can be according to a preselected transient response comprising a maximum and a minimum thermal flux value, $q_{max}$ and $q_{min}$.

Further distinguishing steps include: automatically transferring and controlling an energy input into the central element, and automatically measuring values $T_{High\text{-}1}$ and $T_{High\text{-}1}$ using the computer processor; automatically calculating an "R" value for the material by finding a difference ($\Delta T_{SSmean}$) between a mean steady state value, $T_{SSmean\text{-}High}$, of $T_{High\text{-}1}$ and $T_{High\text{-}2}$ and a mean steady state value, $T_{SSmean\text{-}High}$, of $T_{Low\text{-}1}$ and $T_{Low\text{-}2}$, and dividing this difference ($\Delta T_{SSmean}$) by a steady state thermal flux value, $q_{SSinput}$, representing an energy input; drawing thermal energy outwardly from each of the exterior surfaces of respective side elements; automatically determining at least a mean maximum value, $T_{mean\text{-}Highmax}$, of $T_{High\text{-}1}$ and $T_{High\text{-}2}$ for the maximum temperatures reached during the preselected transient response and a mean min. value, $T_{mean\text{-}Highmin}$, of $T_{High\text{-}1}$ and $T_{High\text{-}2}$ for the minimum temperatures reached during the preselected transient response; automatically calculating a thermal metric (TRF) according to the following expression (which yields a dimensionless result):

$$TRF = \frac{(T_{mean\text{-}Highmax} - T_{mean\text{-}Highmin})}{(q_{max} - q_{min})} * \frac{1}{R}.$$

The preselected transient response can be set to generally simulate the thermal fluctuations in a mammalian body during periods of rest and activity. Calculated TRF and R values can be readily displayed for communication to a user (e.g., by way of display screen) or stored and further transferred to on-site or off-site, remote, data acquisition equipment.

BRIEF DESCRIPTION OF THE DRAWINGS

For purposes of illustrating the innovative nature plus the flexibility of design and versatility of a preferred test apparatus and associated method, the invention can be better appreciated by reviewing any accompanying drawings of the invention (in which like numerals designate like parts, if included). These figures plus the papers attached to the above-identified provisional application authored by the applicants hereof (pertinent portions of which are hereby incorporated herein, by reference) have been included to communicate the features of the innovative apparatus and method of the invention by way of example, only, and are in no way intended to unduly limit the disclosure hereof.

FIG. 3 is a isometric view (created from a digitized black and white photo) of a preferred apparatus of the invention used for simulating a thermally-dynamic environment, illustrating in greater detail the several features that further distinguish the instant invention from known thermal evaluation techniques and associated known instrument designs.

FIG. 4A illustrates the particular material represented in phantom at 18 in FIG. 1 and FIG. 4B illustrates the central element 12 pictured in FIG. 3.

DETAILED DESCRIPTION OF THE PREFERRED EMBODIMENTS

Figure 1:
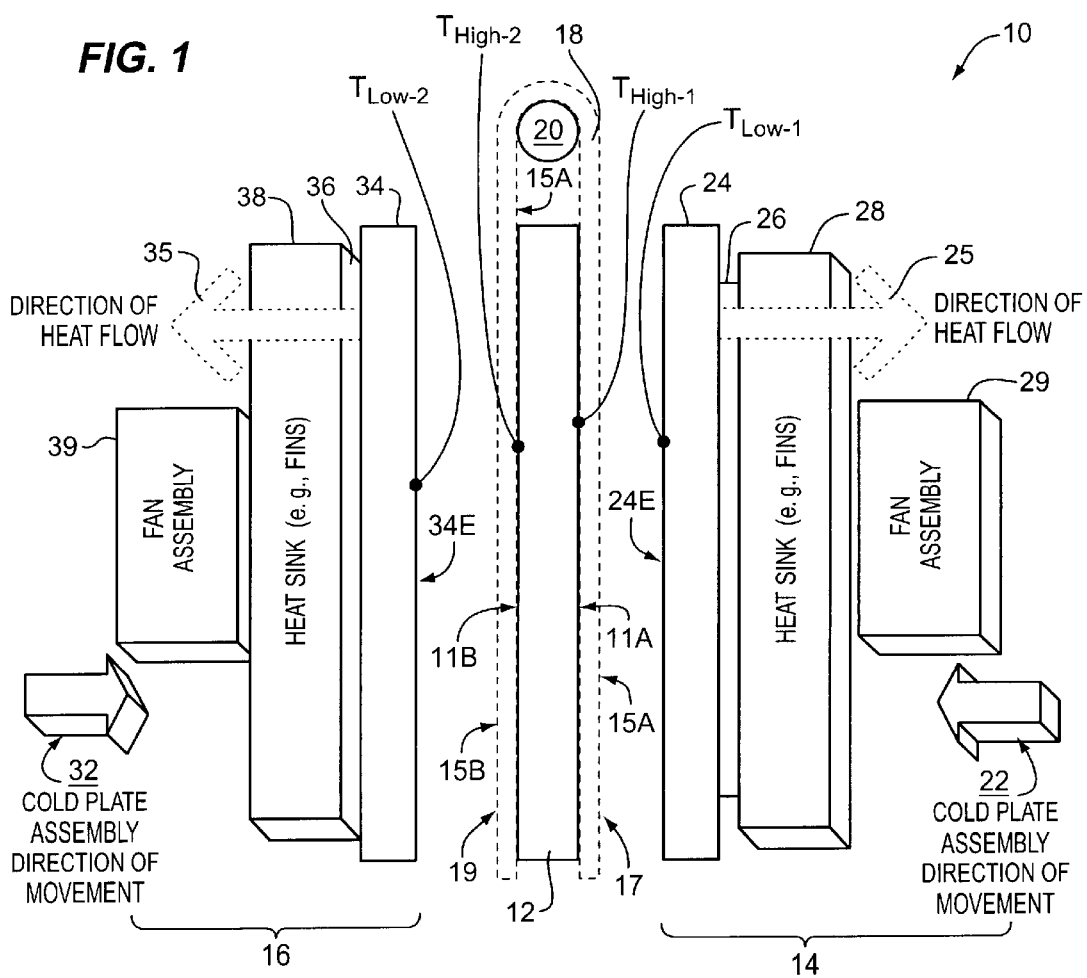
FIG. 1 is a schematic in block-diagram format to illustrate components and features of an apparatus 10 (including, in phantom at 18, the location of a material hung or otherwise supported by support member 20) as contemplated by the invention.
Figure 6:
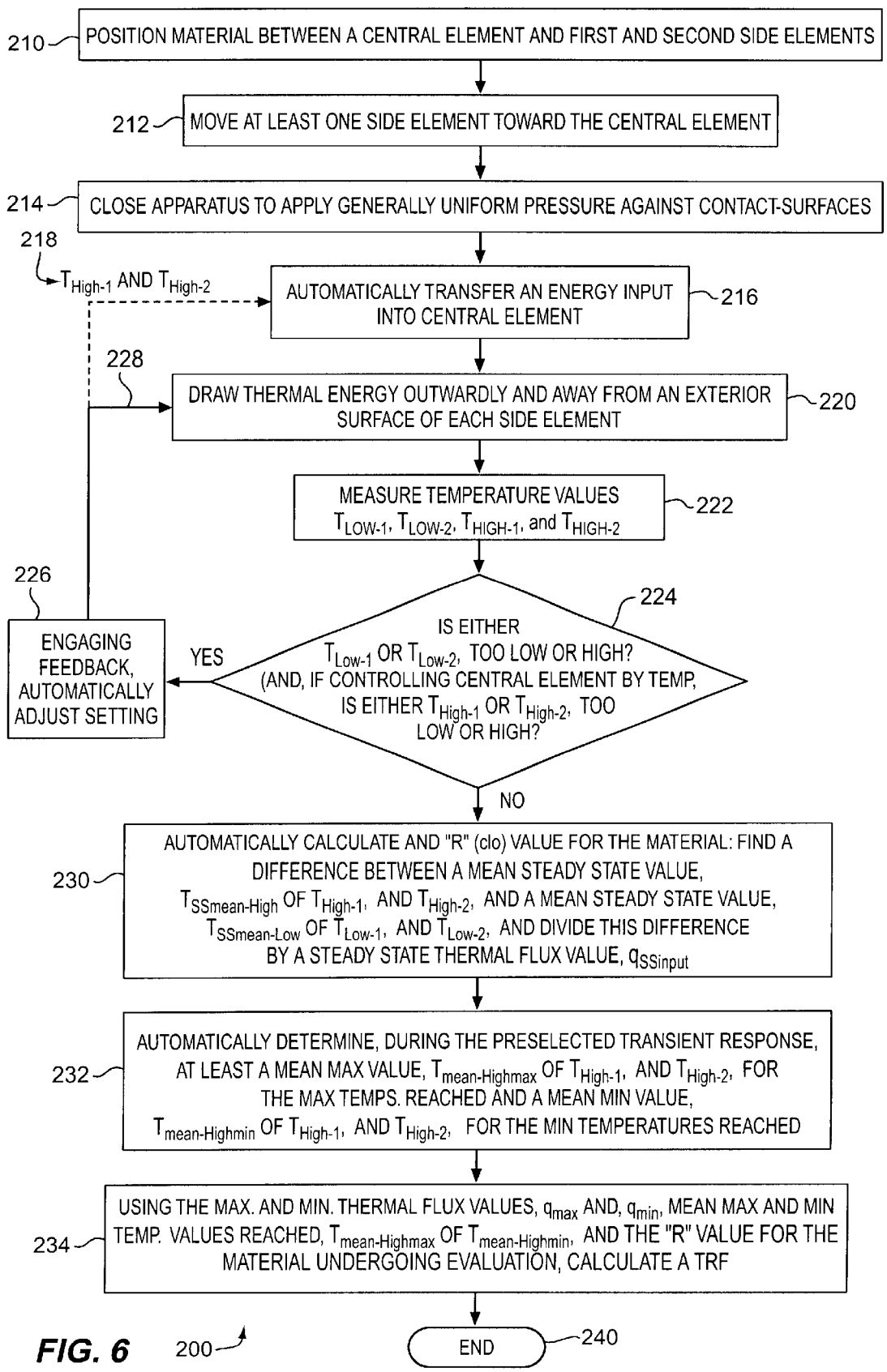
FIG. 6 depicts features of a preferred method of the invention 200, including its additional further distinguishing features, in a detailed flow-diagram format.

The block-schematic of FIG. 1, which is not to scale, represents an apparatus 10 having a central element 12 into which a thermal energy input can be automatically controlled to simulate any actual dynamic environment or microclimate by way of programmed suitable computer processing equipment (see also FIG. 6). Shown hanging from a support rod 20 and draped on either side (outer surfaces 11A, 11B) of element 12 are two side panels 17, 19 of material 18 having an inner-facing contact-surface 15A and an outwardly-facing contact-surface 15B. Thermally-variable cold plate elements 24, 34 are located on either side of central element 12. An exterior surface of each side element, labeled respectively 24E and 34E, face central element 12 so that the apparatus can be moved into a closed position (see FIG. 2) to apply a generally uniform pressure to the contact-surfaces 15A, 15B of material 18. Side elements 24 and 34 are shown as part of cold plate assemblies respectively labeled 14 and 16 which can be moved toward central element 12 in respective directions (arrows 22 and 23). Alternatively, either one of the cold plate assemblies (for example, choose 14) can be moved along either respective direction (again choose 22) toward central element 12, and then that cold plate assembly (14) in contact with material contact-surface 15B (in phantom) draped over the central element 12 can all be moved to contact the other cold plate assembly 16 such that the selected generally uniform pressure is achieved over contact-surfaces 15A, 15B.

Figure 2:
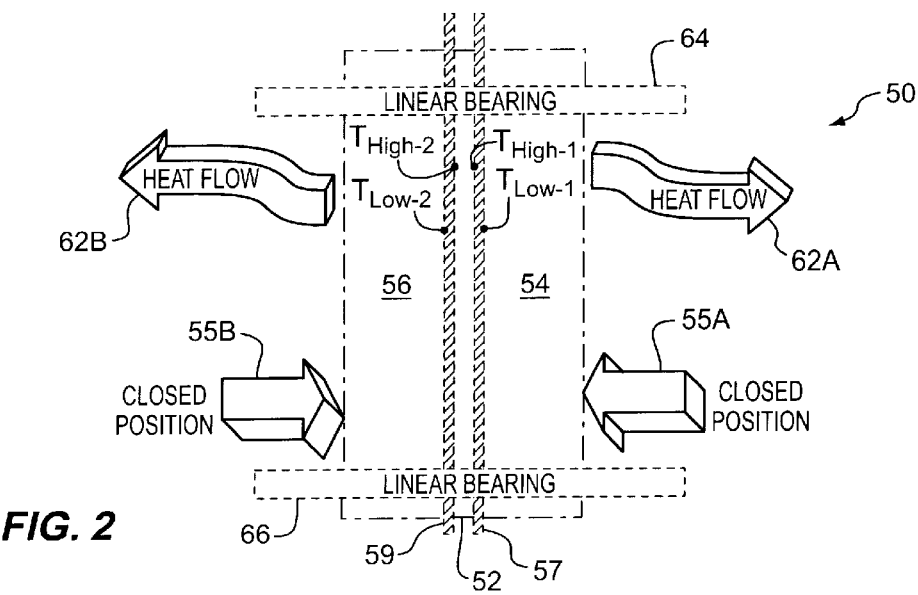
FIG. 2 is a schematic of an apparatus illustrating preferred features of the invention in a 'closed' position with a material put in position for evaluation.

For reference in FIGS. 1 and 2 and as used throughout, surface temperatures of outer surfaces 11A and 11B of central element 12 are identified in FIG. 1, respectively, as $T_{High\text{-}1}$ and $T_{High\text{-}2}$; likewise, surface temperatures of exterior surfaces 24E and 34E are respectively identified as $T_{Low\text{-}1}$ and $T_{Low\text{-}2}$. These temperature values can be measured automatically using any system of suitable temperature sensors including thermocouples, thermisters, platinum resistance temperature detectors (none of which are shown, for simplicity) interconnected with the computer processing unit that can be employed to automatically manage an evaluation performed of a material. Each outer surface 11A, 11B as well as each exterior surface 24E, 34E preferably has more than one temperature sensor to allow temperature measurements to be taken over a larger area of the respective surface, and then averaged, or a mean temperature calculated, for use in making further calculations. Each cold plate assembly 14, 16 has a heat sink and some type of heat pump 26 associated therewith such that, as shown, heat pump 26 is sandwiched between cold plate 24 and heat sink 28 and heat pump 36 is sandwiched between cold plate 34 and heat sink 38 to provide a way to control surface temperatures $T_{Low\text{-}1}$ and $T_{Low\text{-}2}$ as necessary or desired (reference arrows 25 and 35 indicate a preferred general outwardly direction of heat flow away from exterior surfaces 24E, 34E of cold plates 24, 34).

FIG. 2 illustrates an apparatus 50 in a closed position such that it is possible to apply (along the reference directions labeled 55A, 55B) a pressure to the two panels 57, 59 of a material covering respective outer surfaces of thermally-variable element 52. As shown here, cold plate assemblies outlined in FIG. 2 by dashed-boxes 54, 56 and central element 52 are each suitably mounted on an upper and lower linear support bearings 64, 66 (for further detail see FIG. 3). Reference arrows 62A, 62B illustrate the preferred direction of heat flow away from the side assemblies 54, 56 as the apparatus is designed to more-efficiently control the temperatures of the steady state or transient response of the simulated microclimate/environment, to provide more accurate material evaluation results. Central element 52 as well as side assemblies 54, 56 are generally vertically oriented as mounted on linear bearings 64, 66. This allows for greater control over the pressure applied to contact-surfaces of material panels 57, 59, as any affect on such pressure due to gravity is minimal. In an extreme case, as is the case with the horizontally oriented guarded hot plate assembly used in ASTM D 1518 protocol, the underside of the textile being tested due to the mass of the material will add to any compression experienced by that undersurface. The pressure regulator assembly of the apparatus can comprise a simple compression spring assembly, precalibrated using any suitable calibration means (of which there are several) for each material specimen evaluated, to apply a selected pressure against the contact-surfaces of the material once the apparatus is in a closed position. Preferably, the pressure against the contact-surfaces of the material is chosen such that there is contact between the material contact-surfaces and the entire surface area of each outer surface of the central element 52, without compressing the material undergoing evaluation (as material performance is different when a material in a compressed state than in a substantially uncompressed, neutral environment at atmospheric pressure).

The invention will be discussed more-specifically, in connection with the thermo-physiological comfort of garments made of fabrics (of all types): As a human, or any other mammal for that matter, alters its level of activity its level of energy production changes to accommodate. As is well known, any change in energy production within a mammalian body create changes in its level of comfort by either heating or cooling the immediately-surrounding air. Such a system is considered thermally dynamic. As designed and unlike conventional thermal tests and associated testing instruments, the apparatus of the invention more-accurately simulates an actual environment in which a material will be used, especially one as varied as the microclimate between skin and garments and exposed skin and immediately surrounding atmosphere. As mentioned, to better accommodate the thermophysiological comfort of garments, more often they will contain a thermally-dynamic component, or phase change material.

As one can better appreciate by the more-detailed isometric in FIG. 3, the central element comprises a relatively thin flexible heater 12. As shown by way of example here and as represented in FIG. 4B, the flexible heater is quite thin (at 0.010" thick) with a surface area equal to its height (h) times its width (w). The heater at 12 is shown hung from support bar 20, which can likewise be used to support relatively thin material 18 (see also FIG. 4A) of thickness (t) having a surface area equal to its height (h) times its width (w). Preferably, as one can better appreciate in connection with FIGS. 1 and 4B, the surface area of contact-surface 15A is at least equal to the sum total surface area of both outer surfaces 11A, 11B. Central element 12 can, by way of example only, be made of suitably sturdy polymeric material that is pliable; embedded therein or attached or secured thereto is a thermally-conductive foil or flat coil (made out of, for example, a metal alloy) and in communication with a power source (at 111 in FIG. 5) as well as the computer processor and memory employed to automatically control thermal flux into the central element 12. As mentioned, above the heater is a metal rod 20 from which the material specimen may be hung/positioned (such as, for example, a jacket would hang from a human frame). Once again, the material specimen is preferably sized large enough to cover the outer surfaces of central element 12. Positioned in proximity, and on either side of, central element 12 is a cold thermally-conductive plate 24, 34 made out of, for example, an aluminum alloy. These plates 24, 34 are cooled via suitable computerized feedback system which will recognize when surface temperature values fall outside of a selected temperature or range to engage thermoelectric coolers (not labeled for simplicity but sandwiched between the cold plates 24, 34 and heat sinks 28, 38) and/or fan assemblies (one of which can be seen at 29). Thermal energy (in the form of heat) from the cooled plates is circulated via the aluminum heat sinks 28, 38 and moved further from the assembly with a powered rotor or fan (29). As mentioned in connection with FIG. 2, it is critical in the evaluation of a material that can be easily over-compressed (such as a textile), that the pressure applied against the material under evaluation, be controlled. All energy inputs and temperatures can be recorded by a computer data acquisition system for processing. In this manner, one can readily measure temperature variation of a simulated textile-to-skin microclimate given certain test parameters, including level of simulated human activity, environmental conditions, and fabric characteristics (phase change material application, layered systems, etc.).

Theoretical Framework

As is known, heat conduction through a one-dimensional homogeneous material is governed by the following second-order partial differential equation:

$$\frac{\partial^2 T(x, y)}{\partial x^2} = \frac{1}{\alpha} \frac{\partial T(x, t)}{\partial t} \quad [\text{Eq 1}]$$

where  $T$ = the temperature at position $x$,
  $t$ = time
  $\alpha$ = the thermal diffusivity $\frac{k}{\rho C_p}$
  $k$ = thermal conductivity $(\text{W/m}^\circ \text{ K.})$
  $\rho$ = density $(\text{kg/m}^3)$ and
  $C_p$ = specific heat $(\text{J/kg}^\circ \text{ K.})$ The heat flux at any position x and time t is given by:

$$q(x, y) = -k \frac{\partial T(x, t)}{\partial x} \quad [\text{Eq 2}]$$

In both Eq. 1 and Eq. 2, each of k, $\rho$, and $C_p$ are assumed to be constant. Note that although this model does not directly account for inclusion of a phase change component (PCM), it is presumed that a constant and comparably large $C_p$ in the temperature region of the phase change is a reasonable approximation for the energy storage of a PCM in the fabric. This approximation leads to very useful results.

A common approach to finding a solution to the above equations is to use the Laplace transform, which is defined for any transformable function f(t) as:

$$L[f(t)] = F(s) = \int_0^\infty f(t)e^{-st} dt \quad [\text{Eq 3}]$$

The utility of the Laplace transform stems from the following property:

$$L\left[\frac{\partial f(t)}{\partial t}\right] = sF(s) - f(t)|_{t=0} \quad [\text{Eq 4}]$$

Hence, the Laplace transform of Eq. 1 transforms that partial differential equation into an ordinary differential equation:

$$\frac{d^2 T(x, s)}{dx^2} = \frac{1}{\alpha} sT(x, s) \quad [\text{Eq 5}]$$

where T(x,0)=0, the solution of this transformed differential equation is:

$$T(x,s) = A \cos h(x\sqrt{s/\alpha}) + B \sin h(x\sqrt{s/\alpha}) \quad [\text{Eq 6}]$$

One can find the Laplace transform of Eq. 2, again assuming that T(x,0)=0:

$$q(x, s) = -k \frac{dT(x, s)}{dx} \quad [\text{Eq 7}]$$

On differentiation of Eq. 6 with respect to x and substitution into Eq. 7, we have:

$$q(x,s) = -k\sqrt{s/\alpha} A \sin h(x\sqrt{s/\alpha}) - k\sqrt{s/\alpha} B \cos h(x\sqrt{s/\alpha}) \quad [\text{Eq 8}]$$

Consider, now, only the temperature and heat flux at the surfaces of the fabric (at x=0 and x=l where l is the thickness of the fabric in meters). For notational convenience, define new variables as follows:

$$A(s) = \cosh(l\sqrt{s/\alpha})$$

$$B(s) = \frac{1}{k\sqrt{s/\alpha}}\sinh(l\sqrt{s/\alpha})$$

$$C(s) = k\sqrt{s/\alpha}\sinh(l\sqrt{s/\alpha})$$

$$D(s) = \cosh(l/\sqrt{s/\alpha})$$

where $A(s)$ and $B(s)$ should not be confused with A and B used previously. With these new variables, one can write:

$$T_1(s) = A(s)\,T_2(s) + B(s)\,q_2(s),\ B(s) \neq 0 \quad [\text{Eq 9}]$$

$$q_1(s) = C(s)\,T_2(s) + D(s)\,q_2(s) \quad [\text{Eq 10}]$$

Note that these two equations can be solved for any two unknowns in terms of the two knowns that arise from the physical boundary conditions of the problem. For example, if the transforms of temperature variation with time are known for both surfaces, then the fluxes are:

$$q_1(s) = \frac{D(s)}{B(s)}T_1(s) - \frac{1}{B(s)}T_2(s),\ B(s) \neq 0 \quad [\text{Eq 11}]$$

$$q_2(s) = \frac{1}{B(s)}T_1(s) - \frac{A(s)}{B(s)}T_2(s),\ B(s) \neq 0 \quad [\text{Eq 12}]$$

Now extend the treatment of one-dimensional heat flow to include multilayered assemblies. Notice that Eqs. 9 and 10 describe the transform of heat flow and temperature on one surface in terms of the transform of the heat flow and temperature on the other surface. Now rewrite these equations in matrix form as:

$$\begin{bmatrix} T_1(s) \\ q_1(s) \end{bmatrix} = \begin{bmatrix} A(s) & B(s) \\ C(s) & D(s) \end{bmatrix} \begin{bmatrix} T_2(s) \\ q_2(s) \end{bmatrix} \quad [\text{Eq 13}]$$

Suppose now that it is a two-layer garment, where $T_1(s)$ and $q_1(s)$ are the transforms of temperature and flux at the inner surface of fabric 1, and $T_2(s)$ and $q_2(s)$ refer to the interface between fabric 1 and fabric 2. $T_3(s)$ and $q_3(s)$ refer to the outer surface, surface 3. Treat each fabric individually, noting that surface 2 is both the "outside" of fabric 1 and the "inside" of fabric 2, we have for fabric 1:

$$\begin{bmatrix} T_1(s) \\ q_1(s) \end{bmatrix} = \begin{bmatrix} A_1(s) & B_1(s) \\ C_1(s) & D_1(s) \end{bmatrix} \begin{bmatrix} T_2(s) \\ q_2(s) \end{bmatrix} \quad [\text{Eq 14}]$$

and for fabric 2:

$$\begin{bmatrix} T_2(s) \\ q_2(s) \end{bmatrix} = \begin{bmatrix} A_2(s) & B_2(s) \\ C_2(s) & D_2(s) \end{bmatrix} \begin{bmatrix} T_3(s) \\ q_3(s) \end{bmatrix} \quad [\text{Eq 15}]$$

where $$A_1(s) = \cosh(l_1\sqrt{s/\alpha_1})$$

$$B_1(s) = \frac{1}{k\sqrt{s/\alpha_1}}\sinh(l_1\sqrt{s/\alpha_1})$$

$$C_1(s) = k_1\sqrt{s/\alpha_1}\sinh(l_1\sqrt{s/\alpha_1})$$

$$D_1(s) = \cosh(l_1\sqrt{s/\alpha_1})$$

are all dependent on the properties of fabric 1 and the Laplace transform variable, s. $A_2(s)$, $B_2(s)$, $C_2(s)$, and $D_2(s)$ are similarly defined based on the properties of fabric 2.

Now substitute the right-hand side of Eq. 15 for $$\begin{bmatrix} T_2(s) \\ q_2(s) \end{bmatrix}$$

in Eq. 14, yielding:

$$\begin{bmatrix} T_1(s) \\ q_1(s) \end{bmatrix} = \begin{bmatrix} A_1(s) & B_1(s) \\ C_1(s) & D_1(s) \end{bmatrix} \begin{bmatrix} A_2(s) & B_2(s) \\ C_2(s) & D_2(s) \end{bmatrix} \begin{bmatrix} T_3(s) \\ q_3(s) \end{bmatrix} \quad [\text{Eq 16}]$$

For any multilayered ensemble of fabrics one can calculate the so-called "transmission matrix," defined as:

$$\begin{bmatrix} A(s) & B(s) \\ C(s) & D(s) \end{bmatrix} = \begin{bmatrix} A_1(s) & B_1(s) \\ C_1(s) & D_1(s) \end{bmatrix} \begin{bmatrix} A_2(s) & B_2(s) \\ C_2(s) & D_2(s) \end{bmatrix} \begin{bmatrix} A_3(s) & B_3(s) \\ C_3(s) & D_3(s) \end{bmatrix} \ldots \quad [\text{Eq 17}]$$

$$\begin{bmatrix} A_{n-1}(s) & B_{n-1}(s) \\ C_{n-1}(s) & D_{n-1}(s) \end{bmatrix} \begin{bmatrix} A_n(s) & B_n(s) \\ C_n(s) & D_n(s) \end{bmatrix}$$

With $A(s)$, $B(s)$, $C(s)$, and $D(s)$ now redefined as elements of the above overall transmission matrix, the multilayered problem takes the same form as that of a single-layer:

$$\begin{bmatrix} T_1(s) \\ q_1(s) \end{bmatrix} = \begin{bmatrix} A(s) & B(s) \\ C(s) & D(s) \end{bmatrix} \begin{bmatrix} T_{n+1}(s) \\ q_{n+1}(s) \end{bmatrix} \quad [\text{Eq 18}]$$

Write the term of the transmission matrix in terms of the thermal resistance, R, and thermal capacitance, C defined as follows:

$$R_1 = \frac{l_1}{k_1}\ \text{and, in general,}\ R_n = \frac{l_n}{k_n} \quad [\text{Eq. 19}]$$

$$C_1 = l_1\rho_1 C_{p1}\ \text{and, in general,}\ C_n = l_n\rho_n C_{pn} \quad [\text{Eq 20}]$$

Note that clothing insulation is often expressed in terms of the "clo" unit. The relation between R and clo is as follows: R=0.155 clo or 1 clo is equivalent to 0.155 m$^2$ K/W. Notice that $$R_n C_n = \frac{l_n^2}{\alpha_n}.$$

Thus, the single-layer transmission matrix becomes:

$$\begin{bmatrix} A_1(s) & B_1(s) \\ C_1(s) & D_1(s) \end{bmatrix} = \quad [\text{Eq 21}]$$

$$\begin{bmatrix} \cosh(\sqrt{sR_1C_1}) & \frac{R_1}{\sqrt{sR_1C_1}}\sinh\sqrt{sR_1C_1} \\ \frac{\sqrt{sR_1C_1}}{R_1}\sinh(\sqrt{sR_1C_1}) & \cosh(\sqrt{sR_1C_1}) \end{bmatrix}$$

We also note that for a fabric without capacitance:

$$\begin{bmatrix} A_1(s) & B_1(s) \\ C_1(s) & D_1(s) \end{bmatrix} = \begin{bmatrix} 1 & R_1 \\ 0 & 1 \end{bmatrix} \quad [\text{Eq 22}]$$

This means that air layers or other light fabrics can be routinely included in the calculation of the multilayered transmission matrix.

Phase change fabrics used in active wear can be viewed as having an equivalent capacitance so long as the temperature of the fabric is within the phase change region. Recall that in an example where a snow skier is first active then inactive, then active again and so on, one can simulate this with the apparatus by assuming that a sinusoidally varying energy level is applied to the hot plate (element 12) while the cold plates (elements 24, 34) are kept at a constant temperature. The hot plate temperature is measured and the amplitude of the temperature variation about the mean is recorded. For sinusoidally varying boundary conditions, the transmission matrix can be written by simply substituting $j\omega$ for s in equations 21. For a single layer fabric we have:

$$\begin{bmatrix} A_1(j\omega) & B_1(j\omega) \\ C_1(j\omega) & D_1(j\omega) \end{bmatrix} = \begin{bmatrix} \cosh(\sqrt{j\omega R_1 C_1}) & \frac{R_1}{\sqrt{j\omega R_1 C_1}} \sinh\sqrt{j\omega R_1 C_1} \\ \frac{\sqrt{j\omega R_1 C_1}}{R_1} \sinh(\sqrt{j\omega R_1 C_1}) & \cosh(\sqrt{j\omega R_1 C_1}) \end{bmatrix}$$ [Eq 23]

Eq. 18 becomes:

$$\begin{bmatrix} T_1(j\omega) \\ q_1(j\omega) \end{bmatrix} = \begin{bmatrix} A_1(j\omega) & B_1(j\omega) \\ C_1(j\omega) & D_1(j\omega) \end{bmatrix} \begin{bmatrix} T_2(j\omega) \\ q_2(j\omega) \end{bmatrix}$$ [Eq 24]

Casting this in terms of the test apparatus and considering only the sinusoidal portion of the heat transfer (the transient component), $T_1$ is the variation of the hot plate temperature about its mean value, $q_1$ is the sinusoidal variation of the energy into the hot plate about its mean value, $T_2$ is the variation in cold plate temperatures about their mean (zero since the cold plate temperatures are held constant), and $q_2$ is the sinusoidal component of the heat flux at the surface of the cold plates. With $T_2$ equal to zero and elimination $q_2$ from Eq. 24 one gets:

$$T_1(s) = \frac{B_1(s)}{D_1(s)} q_1(s)$$ [Eq 25]

If $q_1$ is a unit sinusoid, then:

$$T_1(t) = \left|\frac{B_1(j\omega)}{D_1(j\omega)}\right| \sin(\omega t - \phi)$$ [Eq 26]

where $$\left|\frac{B_1(j\omega)}{D_1(j\omega)}\right|$$

is the magnitude of this complex quotient and $\phi$ is the phase shift between the flux and temperature sinusoids. If the amplitude of the heat flux qt, is other than unity, then $$\left|\frac{B_1(j\omega)}{D_1(j\omega)}\right|$$

is the ratio of the amplitude of temperature variation to the amplitude of flux variation.
This ratio suggests a way to characterize the temperature regulating ability of phase change fabrics, in particular. The smaller the ratio the better the regulation effect. However, the ratio can only be used when comparing essentially identical fabrics, one with phase change and one without. Normalization is needed. Notice that for steady state ($\omega=0$) or for fabrics with zero capacitance, $$\left|\frac{B_1(j\omega)}{D_1(j\omega)}\right|$$

is equal to the steady state R-value of the fabric (see equation 22).
For fabrics with capacitance, $$\left|\frac{B_1(j\omega)}{D_1(j\omega)}\right|$$

is smaller than the R value for all $\omega$ larger than 0.
The applicants define a new metric called the temperature regulation factor (TRF) by dividing $$\left|\frac{B_1(j\omega)}{D_1(j\omega)}\right|$$

by the steady state R-value for the fabric ($R_1$ for correct notation):

$$TRF = \frac{1}{R_1} \left|\frac{B_1(j\omega)}{D_1(j\omega)}\right|$$ [Eq 27]

which is a dimensionless number less than or equal to one. For fabrics with little or no thermal capacitance the TRF will generally be very close to one. The TRF for a fabric with thermal capacitance will be less than the TRF for a fabric without capacitance. The TRF is an indicator of a fabric's temperature regulating ability whether or not the fabric is a good insulator. Herein, one can calculate R as follows:

$$R = \frac{\Delta T}{Q}$$ [Eq 28]

where $\Delta T = T_{hot} - T_{cold}$
$Q$ = heat flux into the hot plate
$T_{hot}$ = hot plate temp, ° C.
$T_{cold}$ = cold plate temp, ° C.

In connection with FIGS. 4A and 4B—To more accurately evaluate the material, thermal energy losses from the edges of a material undergoing evaluation are preferably keep to a minimum: For example, those materials with an edge surface area that is less than 20%, and even less than 10%, of a total contact area of the central element equal to the sum of the area of each outer surfaces of the central element have better evaluation results.

Figure 5:
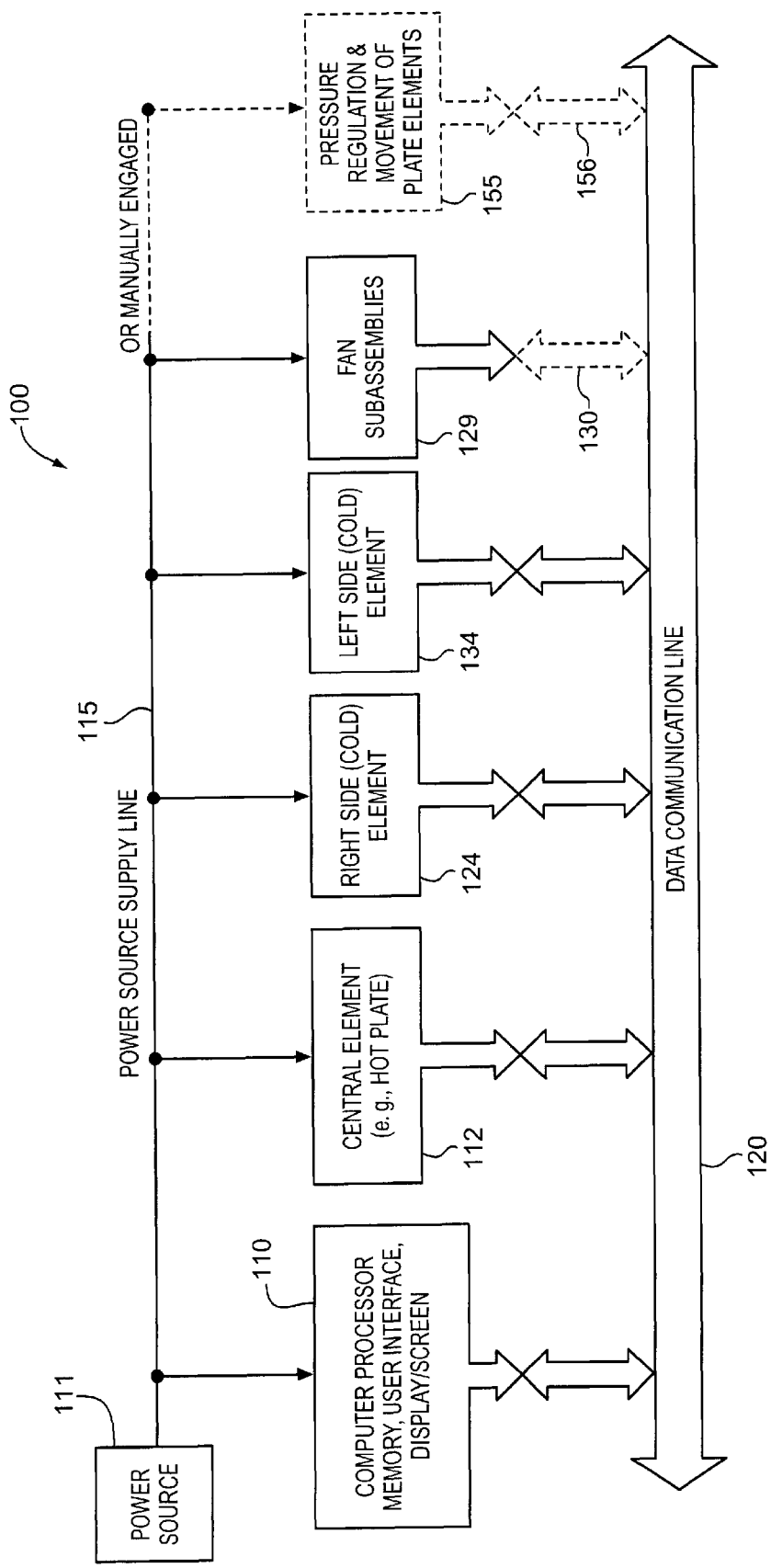
FIG. 5 diagrammatically illustrates intercommunication between components of a preferred apparatus and method of the invention.

Turning, now, to the diagrammatic illustration of a preferred apparatus system 100 in FIG. 5, suitable computer processor interconnected with a user interface and a display screen (which may operate as the user interface, also, in the form of a touch-sensitive display screen) and active memory (110), is preferably in communication with the central element 112, and the right and left side elements 124, 134. One may wish to automatically control the fan assemblies (indicated at 129), although not critical, by providing a communication link (illustrated by way of two way arrow in phantom at 130) between each fan assembly and the computer processor. Likewise, the pressure regulator and lever may be interconnected with the computer processor for automatic control of the movement of the side element(s) and central element to close the apparatus once material has been positioned for evaluation, as represented in phantom at 155 and 156. Power source 111 supplies (via line 115)

electrical energy to power the various devices, if not manually engaged. By way of review, a CPU (Central Processing Unit) is the computing part of a computer: it is made up of the control unit and an arithmetic logic unit (ALU). The CPU, clock and main memory make up a computer. A complete computer system also requires control units, input, output and storage devices and an operating system.

FIG. 6 depicts features of a preferred method of the invention 200 in flow-diagram format. One can readily ascertain novel features thereof by review thereof: The material is positioned 210; at least one side element is moved toward the central element 212; the apparatus is closed 214; an energy input is preferably automatically transferred to the central element 216 (any programmed steady state or transient response may be selected—see callout 217); thermal energy can be drawn away from the exterior surfaces of the side elements 220; selected temperature values can be measured 222; as needed 224 and 226, feedback can be utilized to control any selected surfaces temperatures 228, 218 (in phantom); R values are automatically calculated in steady state, see 230 and callout 231; and for every preselected transient response run, mean or averages can be calculated 232, as well as a TRF; and once done, if no other materials and/or evaluations are needed, the method end is represented at 240.

As explained, the novel evaluation method simulates variable human activity and provides data needed to calculate a temperature regulating factor (TRF) for the fabric. One can simulate based upon certain assumptions about the 'actual' environment then calculate results using the apparatus of the invention, such as: the person wearing a phase change garment (or other thermally-dynamic fabric/material) would be active, then inactive, over a period of 15 minutes (a 15-minute cycle). By way of example only, the hot plate (heater) heat rate would be computer-simulated in a sinusoidal fashion, with a midpoint around 150 W/m² and an amplitude above and below the midpoint of 100 W/m². This example corresponds to a metabolic rate ranging from about 0.9 mets (seated, quiet) to about 4.3 mets (pick and shovel work, tennis).

Each cold plate, in the example describe herein, was maintained at a constant temperature through a feedback controller implemented via customized software (separate feedback loop for each cold plate). The measured cold plate temperatures were compared to a 'desired' temperature and the voltages output to the thermoelectric coolers were varied to maintain a constant temperature. A technician operating the apparatus has the option of selecting the cold plate temperature.

By way of further example, more-specifically, two tests were performed on each fabric evaluated, one to measure the steady-state R value and the other to determine the new metric, TRF. For the R value test, the flux through the hot plate was kept constant, typically at 150 W/m², by setting the amplitude of the sinusoidal variation to zero. The cold plate temperature was kept constant, typically at 10° C. The test was run until the hot plate temperature reached a steady-state constant value. The steady state R value was obtained by dividing the steady state temperature difference by the flux.

For the transient sinusoidal TRF test, it is preferred that the temperature variation of the hot plate be centered about the mid-point of the phase change region for the fabric being tested. This can be accomplished by adjusting the cold plate temperature based on the results of the steady-state test. Two cycles of 15 minutes in length were run (based upon assumptions explained above)—the energy input to the hot plate was varied accordingly. The plate temperature for the second cycle was recorded. During the second cycle, the amplitude of the temperature variation of the hot plate ($T_{max}-T_{min}$) and the amplitude of the flux variation ($q_{max}-q_{min}$) were determined. At the end of the second cycle, the temperature amplitude was divided by the flux amplitude and R value to determine the metric TRF of the system. For example, for fabric C (see Table 1), the maximum temperature ($T_{max}$) reached during the test was 37.38° C. and the minimum temperature was 26.06° C. The maximum flux ($q_{max}$) was 250 W/m² and the minimum flux ($q_{min}$) was 50 W/m². The steady-state R-value was 0.0652° C. m²/W. The TRF was calculated as follows:

$$TRF = \frac{(T_{\max} - T_{\min})}{(q_{\max} - q_{\min})} \frac{1}{R} = \frac{(37.38 - 26.06)}{(250 - 50)} \frac{1}{.0652} = 0.868$$

Table 1 provides information concerning calculated temperature regulating factors (TRF) and R values for fabric with and without phase change material obtained according to the invention.

TABLE 1

| Fabric | Temperature Regulating Factor with Phase Change | Temperature Regulating Factor without Phase Change | Steady State R Value with Phase Change | Steady State R Value without Phase Change |
| --- | --- | --- | --- | --- |
| Fabric A | 0.8704 | 0.8920 | 0.1669 | 0.1552 |
| Fabric B | 0.9255 | 0.9662 | 0.0497 | 0.0543 |
| Fabric C | 0.8680 | 0.9554 | 0.0652 | 0.0677 |
| Fabric D | 0.5207 | 0.7848 | 0.1845 | 0.2013 |
| Fabric E | 0.9532 | 1.0000 | 0.0556 | 0.0619 |
| Fabric F | 0.9203 | 0.9246 | 0.0143 | 0.0189 |

While certain representative embodiments and details have been shown merely for the purpose of illustrating the invention, those skilled in the art will readily appreciate that various modifications may be made to the invention without departing from the novel teachings or scope of this invention. Accordingly, all such modifications are intended to be included within the scope of this invention as defined in any claim following this description. Although the commonly employed preamble phrase "comprising the steps of" may be used herein, or hereafter, in a method claim, the Applicants in no way intend to invoke 35 U.S.C. Section 112 ¶6. Furthermore, in any claim that is filed in connection with this disclosure, any means-plus-function clauses used, or later found to be present, are intended to cover the structures described herein as performing the recited function and not only structural equivalents but also equivalent structures.

What is claimed is:

1. An apparatus for evaluation of a material having a first and second contact-surface, comprising:

a computer-controlled thermally-variable central element comprising a first and second outer surface, at least one outer surface having at least one temperature sensor thereon;

facing said first outer surface is a first exterior surface of a first thermally-variable side element, facing said second outer surface is a second exterior surface of a second thermally-variable side element;

the material adapted to be positioned between said central element's first outer surface and said first exterior surface, and between said central element's second outer surface and said second exterior surface; and a mechanism for moving at least said first exterior surface toward said thermally-variable central element to apply a generally uniform pressure against the material contact-surfaces once the material has been so positioned.

2. The apparatus of claim 1 wherein said first and second outer surfaces have a respective measured temperature value of $T_{High-1}$ and $T_{High-2}$, said first and second exterior surfaces have a respective selected temperature value of $T_{Low-1}$ and $T_{Low-2}$, said thermally-variable central element comprises a relatively flexible plate-like structure oriented generally vertically having a thermally-conductive inner foil in electrical communication with a power source for said thermal-variability.

3. The apparatus of claim 2 wherein said values of $T_{High-1}$ and $T_{High-2}$ are obtained using said temperature sensors, said value of $T_{Low-1}$ is obtained using a third sensor in contact with said first exterior surface, said value of $T_{Low-2}$ is obtained using a fourth sensor in contact with said second exterior surface, and a mean value, $T_{mean-High}$, of $T_{High-1}$ and $T_{High-2}$ is greater than either said selected temperature value $T_{Low-1}$ and $T_{Low-2}$; and further comprising a computer processor in communication with a computer memory for so controlling said central element and for controlling side elements.

4. The apparatus of claim 1 wherein:
said first and second outer surfaces have a respective measured temperature value of $T_{High-1}$ and $T_{High-2}$, said first and second exterior surfaces have a respective selected temperature value of $T_{Low-1}$ and $T_{Low-2}$;
the material is so positioned and said mechanism has been moved whereby the first contact-surface is in contact with said first and second outer surfaces of the central element and the second contact-surface is in contact with said first and second exterior surfaces; and
an edge surface area of the material is less than 20% of a total contact area equal to the sum of the area of each said first and second outer surfaces of the central element.

5. The apparatus of claim 4 further comprising a first heat sink in proximity to a first backside of said first side element, a second heat sink in proximity to a second backside said second side element, and a linear bearing upon which said central element, said first and second side elements, and said respective first and second heat sinks are mounted.

6. The apparatus of claim 5 wherein: said thermally-variable central element comprises a relatively flexible plate-like structure oriented generally vertically; each of said first and second thermally-variable side elements comprises a metal alloy plate-like structure, said respective first and second exterior surfaces of which are contoured to mate with said respective first and second outer surfaces of said central element upon engaging said mechanism for moving; and said mechanism comprises a surface-contact pressure regulator and a lever for moving said first heat sink and said first side element along said linear bearing.

7. The apparatus of claim 6 wherein: the material is a fabric; said pressure regulator is pre-calibrated to said generally uniform pressure; and said relatively flexible plate-like structure comprises a curvature, said respective first and second exterior surfaces contoured to mate therewith, and the material's contact-surfaces likewise contour upon contact with said outer surfaces of said central element and said exterior surfaces of said first and second side elements.

8. An apparatus for evaluation of a material having a first and second contact-surface, comprising:
a computer-controlled thermally-variable central element comprising a first and second outer surface, each said outer surface having at least one temperature sensor thereon;
facing said first outer surface is a first exterior surface of a first thermally-variable side element, facing said second outer surface is a second exterior surface of a second thermally-variable side element, each said exterior surface having at least one temperature sensor thereon;
a first heat sink in proximity to a first backside of said first side element; and
the material adapted to be positioned between said central element's first outer surface and said first exterior surface, and between said central element's second outer surface and said second exterior surface.

9. The apparatus of claim 8 wherein the material has been so positioned and said first and second thermally-variable side elements are also computer-controlled; and further comprising: a first thermoelectric cooler sandwiched between said first side element and said first heat sink, and a second thermoelectric cooler sandwiched between said second side element and a second heat sink; and a mechanism for moving at least said first exterior surface toward said thermally-variable central element is engaged to apply a generally uniform pressure against the material contact-surfaces.

10. The apparatus of claim 8 wherein said first and second thermally-variable side elements are also computer-controlled and said thermally-variable central element comprises a relatively flexible plate-like structure oriented generally vertically; and an edge surface area of the material is less than 20% of a total contact area equal to the sum of the area of each said first and second outer surfaces of the central element; and further comprising a linear bearing upon which said central element and said first and second side elements are mounted.

11. A method of evaluating a material having a first and second contact-surface, comprising the steps of:
positioning the material between a first outer surface, at a temperature $T_{High-1}$, of a computer-controlled thermally-variable central element and a first exterior surface of a first thermally-variable side element, and between a second outer surface, at a temperature $T_{High-2}$, of said central element and a second exterior surface of a second thermally-variable side element;
moving at least one of said side elements toward said central element to apply a generally uniform pressure against the material contact-surfaces; and
measuring a temperature value of said first and second exterior surfaces, respectively $T_{Low-1}$ and $T_{Low-2}$, whereby said temperature values $T_{High-1}$ and $T_{High-2}$ are maintained higher than said temperature values $T_{Low-1}$ and $T_{Low-2}$.

12. The method of claim 11 wherein said step of measuring further comprises automatically controlling said temperature values, $T_{Low-1}$ and $T_{Low-2}$, through feedback carried out using a computer processor; and further comprising the steps of automatically transferring an energy input into said central element, and automatically measuring said temperature values $T_{High-1}$ and $T_{High-2}$ using said computer processor.

13. The method of claim 12 wherein said step of moving further comprises sliding, along a linear bearing, said first side element and a first heat sink in proximity to a first backside of said first side element until said generally uniform pressure is reached; and further comprising the steps of automatically calculating an "R" value for the material by finding a difference ($\Delta T_{SSmean}$) between a mean steady state value, $T_{SSmean-High}$, of $T_{High-1}$ and $T_{High-2}$ and a mean steady state value, $T_{SSmean-Low}$, of $T_{Low-1}$ and $T_{Low-2}$, and dividing said difference ($\Delta T_{SSmean}$) by a steady state thermal flux value, $q_{SSinput}$, representing said energy input.

14. The method of claim 13 wherein said step of automatically transferring an energy input further comprises varying said energy input according to a preselected transient response comprising a maximum and a minimum thermal flux value, $q_{max}$ and $q_{min}$; and further comprising the steps of:

drawing thermal energy outwardly from each of said first and second exterior surfaces of said respective first and second side elements;

automatically determining at least a mean maximum value, $T_{mean-Highmax}$, of $T_{High-1}$ and $T_{High-2}$ for the maximum temperatures reached during said preselected transient response and a mean minimum value, $T_{mean-Highmin}$, of $T_{High-1}$ and $T_{High-2}$ for the minimum temperatures reached during said preselected transient response; and automatically calculating a thermal metric (TRF) according to:

$$TRF = \frac{(T_{mean-High\max} - T_{mean-High\min})}{(q_{\max} - q_{\min})} * \frac{1}{R}.$$

15. The method of claim 11 further comprising the steps of automatically transferring an energy input into said central element according to a preselected transient response, automatically measuring said temperature values $T_{High-1}$ and $T_{High-2}$ and drawing thermal energy outwardly from each of said first and second exterior surfaces of said respective first and second side elements.

16. The method of claim 15 wherein said preselected transient response is one that generally simulates thermal fluctuations in a mammalian body during periods of rest and activity, said step of drawing thermal energy outwardly comprises employing at least one thermoelectric cooler sandwiched between said first thermally-variable side element and a first heat sink and engaging at least one fan rotor; and the material is a sheet material made of at least one layer selected from the group consisting of fabric, fiberglass, drywall, wood, and polymer.

17. The method of claim 15 further comprising the steps of automatically calculating an "R" value for the material by finding a difference ($\Delta T_{SSmean}$) between a mean steady state value of $T_{High-1}$ and $T_{High-2}$ and a mean steady state value of $T_{Low-1}$ and $T_{Low-2}$, and dividing said difference ($\Delta T_{SSmean}$) by a steady state thermal flux value, $q_{SSinput}$, representing said energy input; and displaying said calculated R value.

18. The method of claim 17 wherein said preselected transient response comprises a maximum and a minimum thermal flux value, $q_{max}$ and $q_{min}$; and further comprising the steps of:

automatically determining at least a mean maximum value, $T_{mean-Highmax}$, of $T_{High-1}$ and $T_{High-2}$ for the maximum temperatures reached during said preselected transient response and a mean minimum value, $T_{mean-Highmin}$, of $T_{High-1}$ and $T_{High-2}$ for the minimum temperatures reached during said preselected transient response; and automatically calculating a thermal metric (TRF) according to:

$$TRF = \frac{(T_{mean-High\max} - T_{mean-High\min})}{(q_{\max} - q_{\min})} * \frac{1}{R}.$$

19. The method of claim 18 wherein said step of moving further comprises sliding, along a linear bearing, said first side element toward said central element until contact therewith, and further sliding said first side element and said central element, together along said bearing, toward said second side element until said generally uniform pressure is reached; and further comprising the step of displaying said calculated metric.

20. The method of claim 11 further comprising the steps of:

automatically calculating an "R" value for the material by finding a difference ($\Delta T_{SSmean}$) between a mean steady state value, $T_{SSmean-High}$, of $T_{High-1}$ and $T_{High-2}$ and a mean steady state value, $T_{SSmean-Low}$, of $T_{Low-1}$ and $T_{Low-2}$, and dividing said difference ($\Delta T_{SSmean}$) by a steady state thermal flux value, $q_{SSinput}$, representing an energy input into said central element in a generally steady state;

automatically varying said energy input according to a response comprising a maximum and a minimum thermal flux value, $q_{max}$ and $q_{min}$;

automatically determining at least a mean maximum value, $T_{mean-Highmax}$, of $T_{High-1}$ and $T_{High-2}$ for the maximum temperatures reached during said response and a mean minimum value, $T_{mean-Highmin}$, of $T_{High-1}$ and $T_{High-2}$ for the minimum temperatures reached during said response; and automatically calculating a thermal metric (TRF) according to:

$$TRF = \frac{(T_{mean-High\max} - T_{mean-High\min})}{(q_{\max} - q_{\min})} * \frac{1}{R}.$$

* * * * *